United States Patent [19]

Shirkanzadeh

[11] Patent Number: 5,205,921

[45] Date of Patent: Apr. 27, 1993

[54] METHOD FOR DEPOSITING BIOACTIVE COATINGS ON CONDUCTIVE SUBSTRATES

[75] Inventor: Morteza Shirkanzadeh, Kingston, Canada

[73] Assignee: Queen's University at Kingston, Kingston, Canada

[21] Appl. No.: 650,189

[22] Filed: Feb. 4, 1991

[51] Int. Cl.⁵ .................................................. C25D 11/00
[52] U.S. Cl. ..................................... 205/318; 427/2; 623/16; 204/181.5
[58] Field of Search ............ 623/16; 204/181.5, 180.2; 427/2; 205/318

[56] References Cited

U.S. PATENT DOCUMENTS

| | | | |
|---|---|---|---|
| 3,892,648 | 7/1975 | Phillips et al. | 204/181.4 |
| 4,308,064 | 12/1981 | Takami et al. | 623/16 |
| 4,846,837 | 7/1989 | Kurze et al. | 205/318 |
| 4,880,610 | 11/1989 | Constantz | 623/16 |
| 4,990,163 | 2/1991 | Ducheyne et al. | 427/2 |

*Primary Examiner*—John Niebling
*Assistant Examiner*—Kishor Mayekar
*Attorney, Agent, or Firm*—Richard J. Hicks

[57] ABSTRACT

A process for electro depositing bioactive coatings, such as calcium phosphate or aluminum oxide, onto conductive substrates, such as prosthetic implant devices, is described. An electrolyte bath containing an aqueous solution of the desired oxide or phosphate is prepared with an inert anode such as a platinum anode. A porous or non porous substrate, such as a stainless steel or titanium implant is used as the cathode and a D.C. potential is applied so as to raise the interfacial pH at the cathode sufficient to precipitate the desired oxide or phosphate thereon as a dense adherent film.

14 Claims, No Drawings

METHOD FOR DEPOSITING BIOACTIVE COATINGS ON CONDUCTIVE SUBSTRATES

FIELD OF INVENTION

This invention relates to a process for electro deposition of oxide or phosphate coatings onto conductive substrates and the products thereof. More particularly this invention relates to the electro deposition of bioactive coatings such as calcium phosphate onto implantable prosthetic devices and to the coated product.

BACKGROUND OF INVENTION

It is known that coating prosthetic implant devices such as porous coated orthopaedic prostheses, artificial teeth and the like with an oxide or phosphate coating improves the effectiveness and biocompatibility of the devices, by stimulating bone ingrowth or even bonding chemically to the bone structure. Oxide coatings include alumina and zirconia and phosphate coatings include calcium phosphate (such as $\alpha$ or $\beta$ tricalcium phosphate $Ca_3PO_4$ or $Ca_5(PO_4)_{3-x}(CO_3)_x(OH)_{1+x}$ where x is 0.2 or less) and more particularly calcium hydroxyapatite $Ca_{10}(PO_4)_6(OH)_2$. These coatings are generally of the order of 60 $\mu m$ thick and it has even been suggested that calcium hydroxyapatite (CHA) coatings on hip implants significantly reduces "mid-thigh pain" in the immediate post operative period. CHA coatings are, therefore, the preferred coating and they are generally applied by plasma spraying or by sol-gel processing methods.

Such application methods are not, however, entirely satisfactory. With plasma spraying, which is a "line-of-sight" process it is extremely difficult, if not impossible, to apply a uniform coating to the irregularly shaped surface of a prosthetic device. Furthermore re-entrant and "backface" surfaces cannot be coated at all.

With sol-gel processing, it is somewhat easier to coat irregular surfaces but uniformity remains a problem and these is the problem that the coating must be sintered to remove the organic materials and densify the ceramic material. Local overheating of the metallic substrate may affect the physical properties—such as the fatigue and tensile strengths—of the substrate. Electrophoretic deposition of phosphate films onto titanium substrates also suffers from the fact that sintering of the film is required to provide a uniform adherent coating.

Thus, there is a need for an improved process for the deposition of adherent oxide and phosphate bioactive coatings onto conducting substrates of controlled thickness and porosity which do not require substrate heat treatment or sintering.

OBJECT OF INVENTION

One object of the present invention is to provide an improved process for the deposition of ceramic coatings, particularly oxide and phosphate coatings on porous and nonporous conducting substrates. Another object of the invention is to provide improved coated products.

BRIEF STATEMENT OF INVENTION

By one aspect of this invention there is provided a process for electrodepositing an adherent ceramic coating on a conducting substrate comprising:

(a) providing an electrolytic cell having an inert anode and containing an electrolyte comprising an aqueous "solution containing ions of said ceramic and having a pH of less than 8".

(b) activating said substrate;

(c) immersing said conducting substrate in said electrolyte;

(d) applying a DC potential between said anode and said activated substrate so as to raise the pH of said electrolyte at an interface between said electrolyte and said substrate sufficient to precipitate said ceramic onto said activated substrate.

By another aspect of this invention there is provided a conducting substrate having electro deposited thereon an adherent crystalline coating of a ceramic material.

DETAILED DESCRIPTION OF PREFERRED EMBODIMENTS

According to the present invention, a porous or non porous conductive substrate, such as stainless steel, titanium or titanium alloy implantable prostheses, or more particularly knee or hip replacement prostheses are activated by washing in water, and/or grinding or sand-blasting or etching or ultrasonic cleaning and then immersed in an aqueous solution having a pH of less than about 8, i.e. acid or substantially neutral, which contains ions of the ceramic to be deposited and is preferably an acid solution of about pH4 of calcium phosphate tribasic $(Ca_{10}(OH)_2(PO_4)_6)$ dissolved in hydrochloric acid (about 20g of calcium phosphate/l), as the cathode. Titanium alloys include elements selected from Ta, Nb, Al, V and Pt group metals and combinations thereof. The present invention also contemplates the use of non conducting substrates, such as glass, which are coated with a conducting layer such as Indium Tin Oxide. A platinum anode is also inserted into the solution. A DC potential of between about 0.5 volts and 10 volts and more preferably about 2-3 volts is applied to the electrodes, so as to provide a current density of less than 10 milliamps per sq. cm. The application of a potential cathodically polarizes the substrate and reduces the hydrogen ion concentration at the cathode so that at the surface of the cathode the pH of the solution rises to about pH 8-10 and the desired coating such as aluminum oxide and preferably calcium phosphate is precipitated as a dense, adherent film onto the cathode. Adherent coatings of at least 50 $\mu m$ can be produced at room temperature. As the surface becomes coated with the non conductive coating the electrode becomes progressively more resistive to the passage of the current and the process will eventually stop, thereby limiting the thickness of the film which can be deposited.

Recent evidence indicates that calcium phosphate coatings on prosthetic devices derive their biological activity, in total or in part, by providing a local source of ions essential for bone tissue formation, but immediate incorporation of dissolved Ca and $PO_4$ ions into bone mineral is not necessarily achieved. Radio-labelled $^{45}Ca$ experiments show that only a portion of the dissolved $^{45}Ca$ remains at the implant site, the remainder dilutes the body Ca-pool before incorporation into bone mineral deposits. The effect of increased calcium concentrations is probably not only an effect of mineral precipitation, but also may be a solution-mediated effect on cell proliferation and differentiation. Thus, the density and/or adhesion of the calcium phosphate coatings on the substrate is of secondary importance as the ultimate objective of the present technique is to provide a phosphate coating which will enhance calcified tissue formation within the pores of the metal substrate and the eventual bonding of the tissues to the prosthesis occurs through the mechanical interlock between porous metal and bone.

The electrolyte will contain ions to produce the desired ceramic and may contain Ca, P-containing ions and/or $Zr^{4+}$, $Al^{3+}$, $K^+$, $Na^+$ or ions of platinum group metals and/or other anions such as $\overline{F}$, $CO_3^=$, $HCO_3^-$, $NO_3^-$ or $Cl^-$, depending upon the desired coating. The electrolyte may also contain organic materials such as proteins and biologically non-toxic compounds such as collagen or impurities. The electrolyte may also contain dissolved oxygen.

As the interfacial pH at the cathode is increased, inorganic ceramic compounds (e.g. $Al_2O_3$ or calcium phosphate) may co-precipitate with organic compounds. This process also allows doping of specific ions (e.g. $CO_3^=$ and $\overline{F}$) in calcium phosphate crystals during the nucleation and crystal growth of calcium phosphate compounds.

A characteristic feature of the present invention is that in coating calcium phosphate compounds on Ti or Ti alloy substrates, the calcium phosphate compound is highly crystalline even when the process is conducted at room temperature. It should be noted that for biocompatibility, crystalline calcium phosphate is preferred to an amorphous calcium phosphate. An amorphous calcium phosphate coating according to the prior art is normally subjected to a high temperature hydrothermal process in order to increase its crystallinity and to improve its biocompatibility. The present process eliminates the need for a hydrothermal step, and therefore organic compounds which may be unstable at high temperatures can be co-precipitated with crystalline calcium phosphate compounds. Another characteristic feature of the present invention is that the calcium phosphate coating is composed of an interlocking network of non-orientated crystals with micro pores and that the coating is firmly adhered to the substrate. The coated substrate therefore provides a large surface area of the calcium phosphate crystals in contact with body fluids when used as an implant. It should be noted that a large surface area of calcium phosphate compound is desirable for better chemical and physical interaction between calcium phosphate compound and the biological environment. The micro pores in the calcium phosphate compound coating also encourage better adhesion of, for example, collagen and other bone macro molecules.

For certain applications however, it is preferred to have a dense calcium phosphate coating on a Ti or Ti alloy substrate. This can be achieved by conducting the process under forced flow conditions where there is a relative velocity between the cathode and the electrolyte. This condition can be provided by, for example, stirring the electrolyte in the cell with a magnetic stirrer or by subjecting the electrolyte to ultrasonic vibrations. Alternatively, the coating can be first applied under stagnant condition (Step 1) and then subjected to ultrasonic vibrations for a short period of time, for example, in a methanol bath to remove the loosely adhered crystals (Step 2). By repeating Steps 1 and 2 several times, a dense and firmly adherent coating of calcium phosphate compound can be achieved even at room temperature. Sintering between 300° and 900° C. may also be used to produce a dense coating.

In summary, the nature of the initially precipitated phases and the course of the subsequent crystal growth reaction and crystal morphology is markedly dependent not only upon the degree of saturation and the pH of the electrolyte, but also it is dependent on the applied voltage, ionic strength of the electrolyte, electrolyte temperature, state of the cathode surface, degree of agitation and the types of ions or substance present in the electrolyte. Indeed, the type of phases formed may be influenced by careful control of the physico-chemical conditions.

EXAMPLE 1

An electrolyte was prepared by adding 20 g calcium phosphate tribasic powder ($\approx Ca_{10}(PO_4)_6(OH)_2$) (Aldrich Chemical Company, Inc.) and 58.5g sodium chloride (NaCl) to 1 liter of distilled water. The pH of the electrolyte was adjusted to 4.4 by addition of Hydrochloric acid (HCl). The electrolyte was stirred by a magnetic stirrer for 2 hrs to enhance the dissolution of the calcium phosphate tribasic powder. The electrolyte was then filtered through fine sintered glass filters and transferred to a conventional electrolytic cell having a capacity of 1 liter. The cell was fitted with a commercial saturated calomel electrode (SCE) acting as a reference electrode and a platinum foil acting as the anode of the cell. The surface of a Titanium alloy (Ti 6Al 4V) sample 5 cm long, 1 cm wide and 2 mm thick was roughened on both sides by blasting it with a steel grit (Average particle diameter of 0.5 mm) and then cleaned with methanol in an ultrasonic bath for 15 min. The sample was then washed with distilled water and dried in a stream of air. The sample was then immersed in the electrolyte and used as the cathode of the cell.

The cathode, anode and the reference electrode were then connected to a conventional potentiostat operating under potentiostatic condition and the cathode was polarized to $-1400$ mV with respect to the saturated calomel electrode. No attempt was made to exclude $CO_2$ from the atmosphere entering the cell. This experiment was conducted at room temperature (T=25° C.) for $\frac{1}{2}$ hr and the sample was coated with a layer of calcium phosphate compound.

The sample was then removed from the cell, washed with distilled water and dried in a stream of air for 10 min. Electron microscopic examination of the calcium phosphate coating was carried out using a JEOL-Scanning Electron Microscope (SEM). At relatively high magnification (X10,000) it was observed that the coating had micro pores (pore diameter in the range of 30–50 μm). The coating was composed of an interlocking network of non-oriented platelike crystals (The average size of crystals was $\approx 20$ μm). The chemical analysis of the coating showed that the coating mainly consisted of a $CO_2$-containing calcium phosphate compound with small quantity of Cl, Na and traces of K.

EXAMPLE 2

An electrolyte identical to the electrolyte in Example 1 was used. A Titanium alloy (Ti 6 Al 4V) sample in the form of a rod having a diameter of 0.5 cm and a length of 10 cm was used as the cathode. The sample had a threaded section at one end having a length of 4 cm. The sample was polarized in a similar manner to Example 1, but at $-1300$ mV with respect to the saturated calomel electrode. This experiment was run at an electrolyte temperature of 65° C. for $2\frac{1}{2}$ hrs. SEM examination of the coated sample revealed that the coating structure comprised an interlocking network of fine and plate-like crystals in the range of 2–5 μm in size. The coating also had fine micro pores of the order of 2–5

μm. The coating was continuous and uniform and firmly adhered to the substrate. The chemical analysis of the coating showed that it mainly consisted of a $CO_2$-containing calcium phosphate compound with small amount of Cl. Sodium and potassium were not detectable.

EXAMPLE 3

An electrolyte identical to that of Example 1 was prepared. A Titanium alloy (Ti 6Al 4V) sample similar to that of Example 2 was used as the cathode. The sample was polarized at $-1500$ mV (Vs SCE) in the electrolyte for ½ hr at 25° C. (Step 1). The sample was then removed and subjected to ultrasonic vibration in a methanol bath for 2 min (Step 2). Steps 1 and 2 were repeated alternatively five times. The calcium phosphate coating obtained was fully dense with no porosity. The coating was also continuous, crystalline with very good adhesion to the substrate.

EXAMPLE 4

An electrolyte identical to that of Example 1 was prepared. A Titanium alloy (Ti 6Al 4V) sample with the same dimensions as in Example 1 was mechanically ground. The sample was coated for ½ hr at $-1400$ mV (V$_5$ SCE), 25° C. The coating was then sintered at 350° C. A fully dense coating of calcium phosphate compound with good adhesion to the substrate was obtained. The coating was uniform and had a thickness of $\approx 50$ μm. SEM examination showed that the calcium phosphate crystals were sintered together and that the coating was without any pores.

EXAMPLE 5

Titanium wire having a diameter of 0.3 mm was used to make a three dimensional porous substrate having pores in the range of 500 μm. An electrolyte similar to that in Example 1 was prepared and the porous substrate was coated according to the procedure used in Example 3. The calcium phosphate coating obtained was uniform, crystalline and was strongly bonded to the porous substrate.

I claim:

1. A process for electrodepositing an adherent ceramic phosphate coating on a conducting substrate comprising:
   (a) providing an electrolytic cell having an inert anode and containing an electrolyte comprising an aqueous solution containing ions of said ceramic and having a pH of less than 8;
   (b) activating said conducting substrate;
   (c) immersing said conducting substrate in said electrolyte;
   (d) applying a DC potential between said anode and said activated conducting substrate so as to raise the pH of said electrolyte at an interface between said electrolyte and said activated conducting substrate sufficient to precipitate said ceramic from said electrolyte and onto said activated conducting substrate.

2. A process as claimed in claim 1 wherein said phosphate coating is a calcium phosphate compound coating.

3. A process as claimed in claim 3 when said phosphate coating is selected from the group consisting of $\alpha$ and $\beta$ tricalcium phosphate and components having a formula $Ca_5(PO_4)_{3-x}(CO_3)_x(OH)_{1+x}$ where x is 0.2 or less.

4. A process as claimed in claim 1 wherein said conducting substrate is selected from stainless steel, titanium and alloys thereof, and a non conducting substrate coated with a conducting layer.

5. A process as claimed in claim 4 wherein said non conducting substrate is glass and said conducting layer thereon is indium-tin oxide.

6. A process as claimed in claim 4 wherein said anode is a platinum anode.

7. A process as claimed in claim 1 wherein said DC potential is in the range of 0.05–10 volts, so as to provide a current density of less than 10 milliamps/sq cm.

8. A process as claimed in claim 4 wherein said conducting substrate is selected from a porous substrate and a non porous substrate.

9. A process as claimed in claim 1 including at least one step selected from the group consisting of (a) conducting said process under forced flow conditions (b) subjecting said coated substrate to ultra sonic vibrations and (c) sintering said coated substrate between 300° and 900° C., so as to produce a densified coating.

10. A process as claimed in claim 1 wherein said electrolyte additionally contains ions selected from fluoride, chloride, carbonate, bicarbonate, nitrate, Pt-group metals, dissolved oxygen and carbon dioxide.

11. A process as claimed in claim 10 wherein said electrolyte additionally contains collagen or organic biologically non-toxic compounds.

12. A conducting substrate having deposited thereon a uniform micro-porous, adherent, coating of a ceramic material comprising an interlocking network of non-oriented crystals made by the process of claim 1.

13. A coated substrate as claimed in claim 12 wherein said coating is doped with $CO_3$ ions.

14. A coated substrate as claimed in claim 12 containing co-precipitated biologically active compounds.

* * * * *